United States Patent [19]

Beraha et al.

[11] Patent Number: 4,776,346

[45] Date of Patent: Oct. 11, 1988

[54] BIOPSY INSTRUMENT

[76] Inventors: Dan Beraha, 912 Woodbriar Ct., Fort Walton Beach, Fla. 32548; Alex G. Bersin, 1 Weston Ct., Streamwood, Ill. 60107

[21] Appl. No.: 863,596

[22] Filed: May 14, 1986

Related U.S. Application Data

[63] Continuation-in-part of Ser. No. 579,158, Feb. 10, 1984, Pat. No. 4,600,014.

[51] Int. Cl.⁴ ............................................. A61B 10/00
[52] U.S. Cl. ..................................................... 128/754
[58] Field of Search ................................. 128/749–752, 128/753, 754

[56] References Cited

U.S. PATENT DOCUMENTS

| | | | |
|---|---|---|---|
| 3,561,429 | 2/1971 | Jewett et al. | 128/752 |
| 4,178,810 | 12/1979 | Takahashi | 128/751 |
| 4,393,872 | 7/1983 | Reznik et al. | 128/752 |
| 4,396,021 | 8/1983 | Baumgartner | 128/753 |
| 4,522,206 | 6/1985 | Whipple et al. | 128/752 |
| 4,542,749 | 9/1985 | Caselgrandi et al. | 128/752 |
| 4,600,014 | 7/1986 | Beraka | 128/754 |
| 4,617,940 | 10/1986 | Wang | 128/754 |
| 4,699,154 | 10/1987 | Lundgren | 128/754 |
| 4,702,261 | 10/1987 | Cornell et al. | 128/754 |

FOREIGN PATENT DOCUMENTS

| | | | |
|---|---|---|---|
| 10321 | 4/1980 | European Pat. Off. | 128/754 |
| 175611 | 3/1966 | U.S.S.R. | 128/754 |
| 1009419 | 4/1983 | U.S.S.R. | 128/749 |

Primary Examiner—Lee S. Cohen
Assistant Examiner—David Shay
Attorney, Agent, or Firm—Macdonald J. Wiggins

[57] ABSTRACT

An improved instrument for obtaining tissue samples for biopsies is adapted to permit accurate samples to be taken with one-hand. The instrument includes a housing which fits into the palm of the physician's hand and has a guide tube projecting from the forward end which the physician guides to a point from which a sample is required. A spring-loaded cannula is telescoped within the guide tube and a notched sampling stylet is telescoped within the cannula. The tips of the cannula and stylet project slightly from the distal end of the guide tube. An arming slide is provided which is moved forward by the physician's thumb, advancing the stylet into the tissue and cocking the spring-loaded cannula. The physician's thumb then operates a spring release trigger causing the cannula to snap forward, cutting the tissue sample in the stylet notch. The instrument is then withdrawn from the tissue.

4 Claims, 3 Drawing Sheets

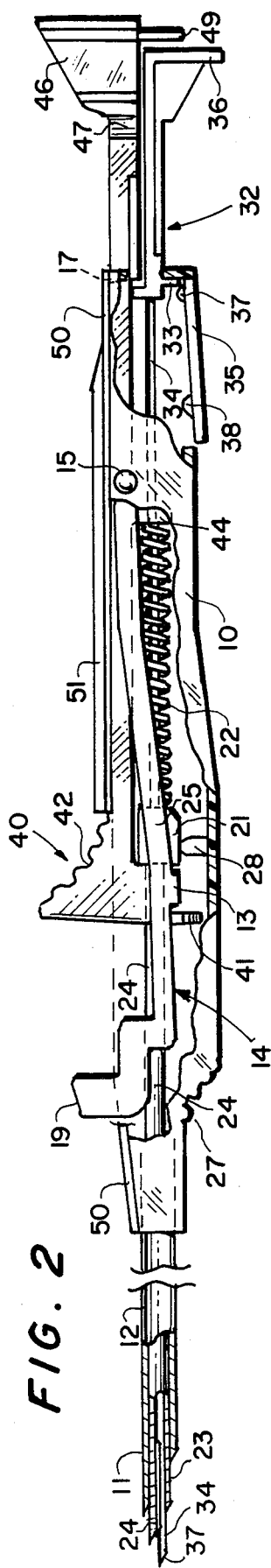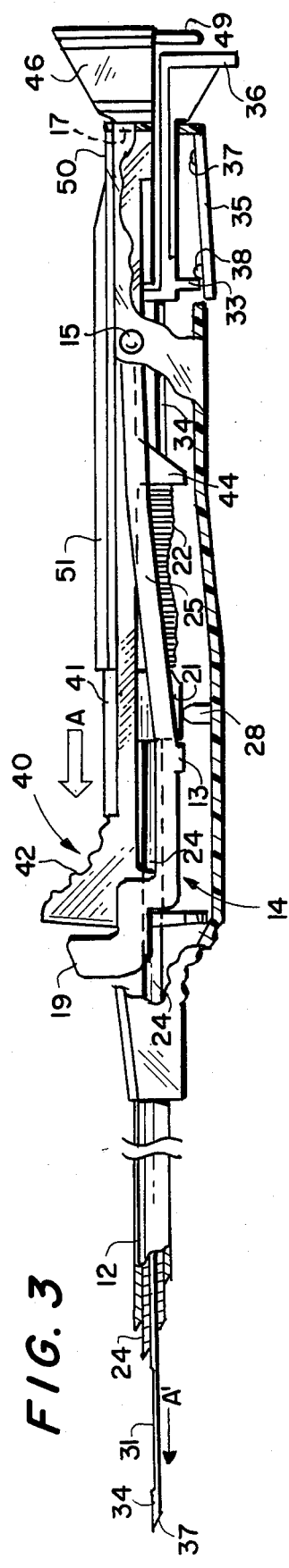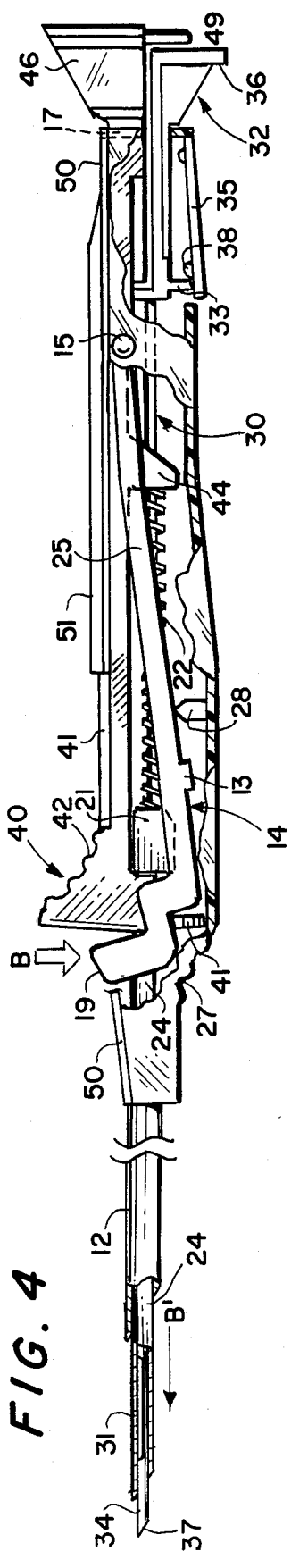

FIG. 5  FIG. 6  FIG. 7
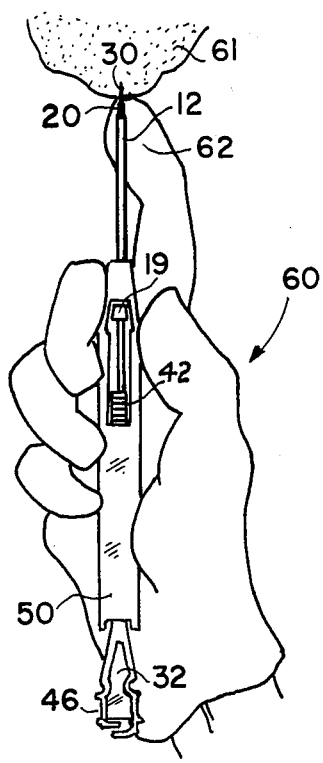
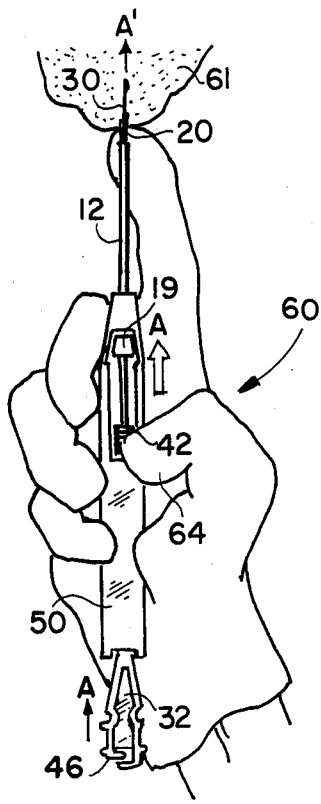
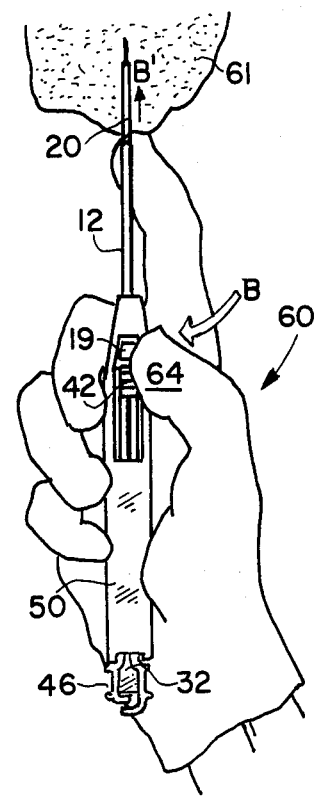
FIG. 8  FIG. 9
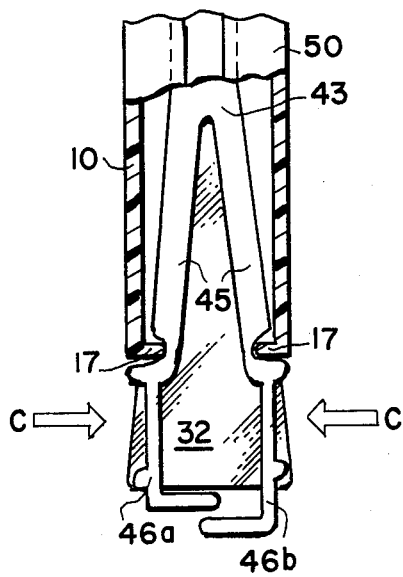
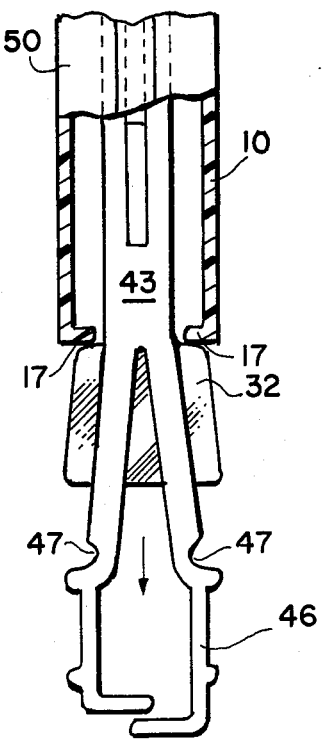

BIOPSY INSTRUMENT

This application is a continuation-in-part of co-pending application, Ser. No. 579,158 now U.S. Pat. No. 4,600,014.

BACKGROUND OF THE INVENTION

1. Field of the Invention

The present invention relates to an improved biopsy instrument and more particularly to a medical instrument that permits a clean margin core of tissue to be obtained with the physician using one hand to control the instrument.

2. Description of the Prior Art

In performing procedures for obtaining tissue samples, there have existed problems in obtaining diagnostic material adequate for definitive interpretation by a qualified pathologist. Using the case of obtaining samples of tissue for the diagnosis of malignancies of the prostate gland as an example, it is known to utilize cytologic studies based on a fine needle aspiration biopsy. For example, a device for this purpose is disclosed in U.S. Pat. No. 3,595,217 to Rheinfrank. A hollow biopsy needle is passed through a guide tube attached to the operator's finger which is placed on the prostate gland. The needle penetrates the gland and a syringe attached to the needle withdraws a tissue sample. Unfortunately, the use of an aspirating needle to obtain samples from the prostatic tissue has not, in general, produced satisfactory diagnostic material and this approach has been largely abandoned in the United States.

Consequently, a preferred approach is to obtain a core sample. Many physicians utilize a biopsy needle available from Travenol Laboratories, Inc. of Deerfield, Ill. and described in U.S. Pat. No. 3,477,423 to Griffith. The Travenol TRU-CUT$^R$ biopsy needle comprises a hollow tubular cutting cannula having a sharpened distal end attached to a plastic handle. A coaxial solid stylet telescopes within the cannula and is attached to a knob at its proximal end. The distal end of the stylet is sharpened and includes a transverse slot or specimen notch adjacent to the sharpened end.

In the prostatic sample example, the physician positions the stylet of the Travenol needle to project slightly from the cannula. The index finger of one hand is placed along the cannula with the tip in contact with the stylet distal end and the handle is held in the palm. Approaching the prostate gland transrectally, the gland is explored with the finger tip to locate a nodule or suspicious area. After locating a point for a sample, the needle is cased forward into the nodule. Once in place, the stylet is plunged to the desired depth.

The physician must then remove his hand and finger, grasp the stylet knob in one hand, and push the cannula handle forward with the other hand. Theoretically, the cutting end moves along the stylet and severs a sample of tissue projecting into the transverse slot in the tip of the stylet. The entire needle is then withdrawn from the gland and the sample removed from the stylet.

In practice, the manipulation of the cannula during this latter step is quite difficult since the tip of the stylet is embedded in the soft and pliable prostatic tissue several inches from the handle. The stylet knob gives very little steady support to the needle assembly and the stylet tip, due to its smaller diameter, penetrates the tissue somewhat easier than the tubular cannula cutting edge. On occasions, when attempting to push the cannula into the tissue, the entire needle moves forward, puncturing the bladder or uretha. It is also common to attempt to move the cannula forward only to have the stylet back out of the tissue. When this occurs, the physician must remove the needle, reposition the stylet, and try again.

Since the procedure involves puncturing of the colon wall, each attempt increases the risk of infection. Most physicians limit such attempts to two or three passes. Even with a successful insertion of the cannula, the instability of the Travenol needle often results in a limiting core sample. Similar problems exist in obtaining biopsies of other organs.

Other biopsy devices are known. For example, Russian Pat. No. 400,319 teaches a needle having an adjustable depth device and obtains a sample by suction. Drer, European Pat. No. 10,321 discloses a one-handed instrument suitable for taking a biopsy of yieldable tissue using a spring driven cannula. Baumgartner in U.S. Pat. No. 4,396,021 describes a biopsy instrument designed to be inserted into a standard cystoscopic instrument and must be guided visually.

In my co-pending application, Ser. No. 579,158 entitled "Transrectal Biopsy Device", I disclose an improved instrument of the Griffith-type which permits the physician to guide the needle to the exact point required for a sample by means of a guide tube and to thereafter maintain that hand and finger in place during the remainder of the sampling procedure, eliminating the problems in using the Griffith-type needle noted above.

In that invention, the operator can accurately and safely perform the sampling procedure. However, the unit requires the use of one hand to hold the needle in position and the other hand to operate the stylet and cannula for obtaining a sample of tissue. It is desirable that the sampling procedure be accomplished using the same hand holding the instrument in place. Thus, the other hand of the physician is free to steady the patient during the critical sampling period.

Thus, there is a long-felt and unfilled need for a biopsy needle which can be guided to the required point of the prostate gland by the physician's finger, a sampling stylet inserted, and a cutting cannula plunged forward without removal of the finger and which would permit the entire procedure to be completed using one hand.

SUMMARY OF THE INVENTION

The present invention is a further improvement in a biopsy sampling instrument which is especially suited for transcrectal prostate biopsies, although the device is also applicable to many other biopsy procedures. Through the use of a novel spring loading and releasing structure, the physician can perform the entire procedure with one hand. The spring loading arrangement eliminates approaching the patient with a cocked instrument and the attendant risk of premature release which could cause injury. A rapid cutting of the sample core resulting from spring loading of the cannula produces cleaner margins of the sample than obtainable with known prior art instruments.

A housing is provided which is adapted to be held in the palm of the operators hand. The housing includes a forward guide tube having a spring loaded cannula telescoped therethrough. A stylet assembly is telescoped within the cannula and includes a hub which extends from the rear of the housing. The stylet projects slightly from the cannula and guide tube, and includes a sampling notch at its distal end.

An arming slide is movable in the housing by means of a thumb tab projecting from the top of the housing. When the arming slide is moved fully forward, the stylet is fully extended from the cannula and guide tube and the cannula spring is cocked. A release trigger is provided near the forward end of the housing which is depressed to release the spring loaded cannula for slicing tissue in the stylet sampling notch.

To use the instrument, the physician holds it in the palm of the hand with the index finger at the tip of the guide tube. The tip of the stylet is thereby guided to the point at which a sample is to be obtained. The physician then moves the arming slide fully forward with the thumb, causing the stylet tip to penetrate the tissue such that tissue expands into the notch. The movement also cocks the cannula spring. The operator then depresses the release trigger causing the sharpened cannula to snap forward, cleanly slicing the tissue in the stylet notch.

The instrument is then withdrawn from the tissue and the sample is removed.

It is therefore a principal object of the invention to provide an improved biopsy instrument in which the physician can guide the tip of a sampling stylet to a desired location using the index finger, advance a sampling stylet and cock a spring loaded cannula, and thereafter operate a trigger to slice a tissue sample with such procedure being performed with the use of one hand.

It is another object of the invention to provide an improved biopsy instrument for one-handed operation having a spring loaded cannula to insure a biopsy tissue sample having very clean margins.

It is yet another object of the invention to provide an improved biopsy instrument in which the index finger of the physician is maintained in contact with the point of sampling during the entire sampling procedure.

These and other objects and advantages of the invention will become apparent when read in conjunction with the drawings.

BRIEF DESCRIPTION OF THE DRAWINGS

FIG. 2 is a partially cut away side view of the device in the condition for approaching a site for a biopsy;

FIG. 3 is the device of FIG. 2 in which the stylet portion has been advanced and the cannula portion has been cocked;

FIG. 4 is the device of FIG. 3 in which the trigger has been actuated and the cannula extended by means of a spring to effect a sampling of tissue;

FIGS. 5, 6, and 7 show the manner of accomplishing the operations of the device shown in FIGS. 2 through 4 with the operator using one hand;

FIG. 8 is a partial view of the proximal end of the device showing the arming slide thereof in a locked position; and FIG. 9 shows the arming slide of FIG. 8 withdrawn for retracting the cannula.

DETAILED DESCRIPTION OF THE PREFERRED EMBODIMENT

Figure 1:
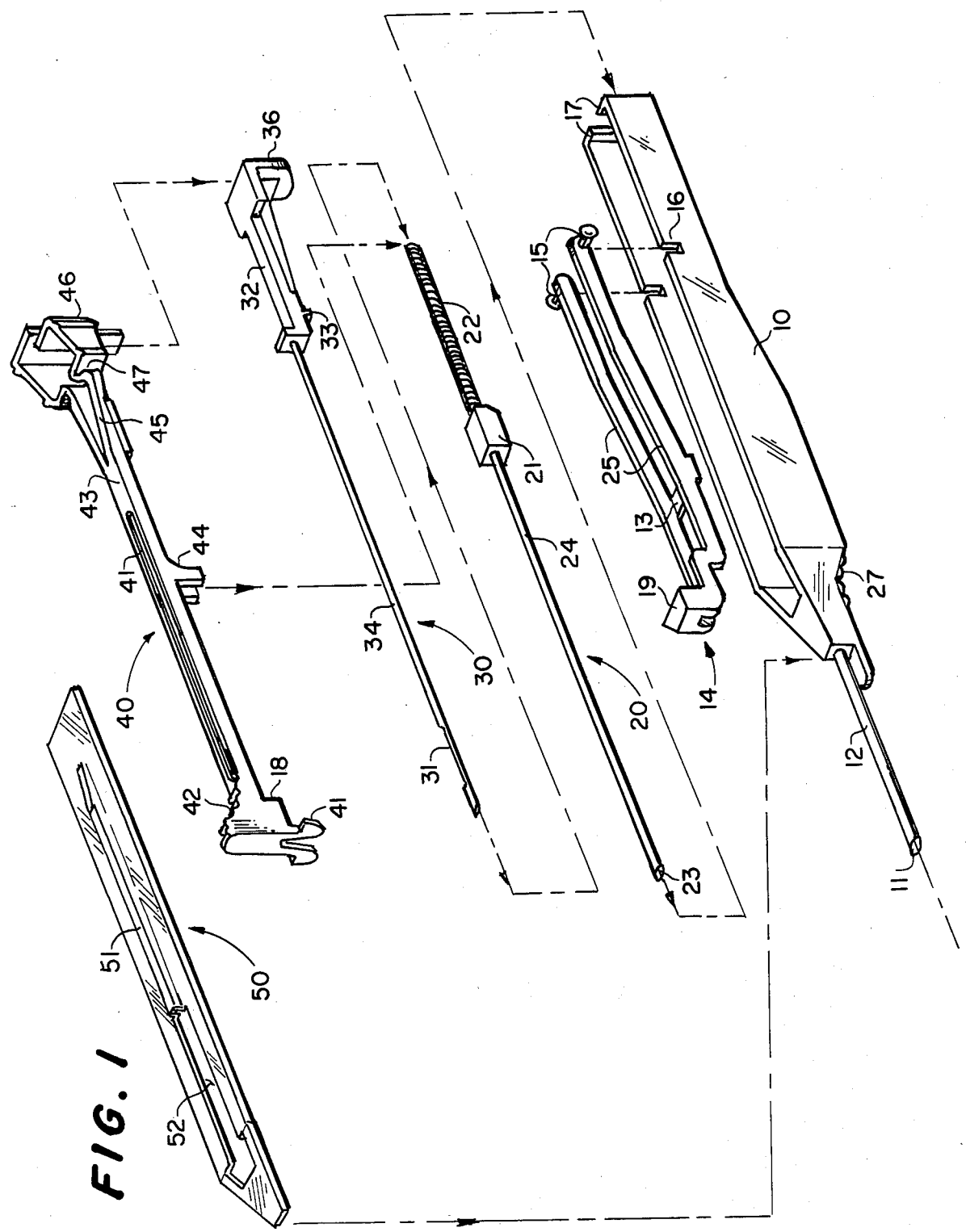
FIG. 1 is an exploded view of the improved biopsy needle of the invention.

The biopsy device of the invention is preferably implemented as a one-use disposable instrument. Referring to FIG. 1, an exploded view of a disposable implementation of the invention is shown. An elongated lower housing 10 is provided preferably formed from a suitable hard plastic. Housing 10 has a guide tube 12 rigidly attached to its distal end. Guide tube 12 is preferably formed from stainless steel and is a thin, tubular element having a sharpened distal end 11. Housing 10 includes an embossed finger grip area 27 near the distal end of housing 10. Housing 10 includes a pair of notches 16 for mounting a release spring 14 as described below. A pair of arming slide locking tabs 17 is provided at the proximal end of housing 10.

A cannula assembly 20 is shown having a cannula hub 21 with a cannula 24 rigidly connected thereto. Cannula 24 is preferably formed of stainless steel and includes a sharpened distal end 23. A cannula spring is engaged to the rear of cannula hub 21. As indicated by the dashed lines, cannula 23, upon assembly, is inserted through guide tube 12 and is extendable therefrom.

Release spring 14 is preferably formed from a resilient plastic and includes a pair of spring arms 25, a pair of rectangular mounting studs 15, a release trigger 19 and a hub stop 13. As indicated by the dashed lines, mounting studs 15, have their rectangular portions inserted into notches 16 in lower housing 10, holding the ends thereof rigid. As will now be understood, pressure on release trigger 19 will, due to the resilience of spring arms 25, permit the trigger 19 to be pushed downward a short distance. As will be described in more detail hereinafter, hub stop 13 acts as a stop to cannula hub 21 during a sequence of operation in which cannula spring 22 is thereby held in a compressed state.

Stylet assembly 30 is shown having a stylet hub 32 from which stylet 34 projects. Stylet 34 includes a sampling notch 31 in its distal end. Stylet hub 32 includes a detent tab 33 and a stylet push bar 36. As indicated by the dashed lines, the distal end of stylet 34 is inserted through cannula spring 32, cannula hub 21 and cannula 24, and is extendable from distal end 23 of cannula 24. As will be later shown, stylet hub 32 extends from the proximal end of lower housing 10 and may be moved forward by stylet push bar 36 until detent tab 33 engages detent 38 of detent flap 35.

Arming slide 40 includes a grip portion 42 and a release trigger lock 48 at the distal end thereof, and a pair of cannula release grips 46 at the proximal end thereof. A slide bar 43 is disposed between cannula release grips 46 and grip 42, and has a pair of cannula spring blocks 44 depending from the central portion thereof. A guide bar 41 is provided along the top surface of slide bar 43. Cannula release grips 46 extend from spring arms 45 and have a stylet push tab 49 depending therefrom and a pair of locking grooves 47. As indicated by the dashed lines, cannula spring blocks 44 engage the proximal end of cannula spring 22 when the parts are assembled in lower housing 10.

When arming slide 43 is assembled in lower housing 10, as will be shown in more detail hereinafter, locking grooves 47 will engage cannula locking tabs 17 in a certain aspect of operation of the instrument. After assembly of the various elements in lower housing 10 as described, upper housing 10 is attached to the top surfaces of lower housing 50 with release trigger 19 and grip 42 of arming slide 40 extending through opening 52 therein and guide bar 41 engaging arming slide guide slot 51.

The assembly of the elements shown in FIG. 1 is more clearly seen from FIGS. 2–4. In FIG. 2, a view of lower housing 10 partially cut away is provided to disclose the various working elements. The instrument is shown in the condition ready for performance of a biopsy procedure. As will be understood with reference to FIG. 1 and the drawings of FIGS. 2-4, the instrument includes a guide tube 12 having a sharpened end 11 with cannula 24 disposed within guide tube 12 and telescoping with respect thereto. Cannula 24 includes a cutting end 23. Stylet 34 is telescoped within cannula 24, and includes cutting end 37 and sampling notch 31. Stylet 34 is slidable within cannula 24 and cannula 24 is slidable within fixed guide tube 12. Cannula 24 is attached to cannula hub 21 while stylet 34 is attached at its proximal end to stylet hub 32. It will be noted from FIG. 2 that a plastic detent flap 35 is molded into the lower portion of the proximal end of lower housing 10 and, provides a pair of detents 37 and 38. Due to the resilience of the material from which housing 10 is formed, detent flap 35 acts as a spring.

In FIG. 2, stylet hub 32 has been withdrawn from housing 10 until detent bar 33 of the stylet hub 32 engages detent 37. This results in stylet 34 being withdrawn as far as possible into cannula 24. The cutting end 37 of stylet 34 extends slightly from cannula 24 and, as will be discussed below, permits the point to be pushed into the tissue during a biopsy procedure. When stylet hub 32 is fully withdrawn from housing 10, arming slide 40 is also fully withdrawn. Arming slide 40 is free to slide along the top surface of stylet hub 32 within guide slot 51 and along the upper surface of cannula hub 21. When arming slide 40 is moved forward, contacting stylet push tab 49 compressing spring 22 as discussed below. A guide block 28 is molded in the bottom surface of lower housing 10 to provide support to cannula hub 21 when in the position of FIG. 2.

When arming slide 40 is in the full rearward position as in FIG. 2, spring 22 is fully extended in a first rearward position with the rear portion of spring 22 contacting spring blocks 44 of arming slide 40. When the physician approaches the tissue to be sampled with the instrument in the condition shown in FIG. 2, spring 22 is relaxed and the tip of stylet 34 is projecting slightly from cannula 24. The physician will locate the desired point on the tissue and will penetrate the tissue with the cutting tip 37 of stylet 34. At this point, it is required to insert the stylet to the desired depth in the tissue and this is accomplished by moving arming slide 40 forward as indicated in FIG. 3 by arrow A. Slide 40 may be moved forward by pressure on grip 42 in the direction of arrow A. This causes cannula release grips 46 to move forward until locking grooves 47 engage locking tabs 17 in lower housing 10. At the same time, cannula spring blocks 44 compress cannula spring 22 with cannula hub 21 bearing against hub stop 13 of release spring 14. When locking grooves 47 engage locking tab 17, spring 22 and cannula 24 are then in the cocked position.

As previously mentioned, moving arming slide 40 forward also extends stylet 37 since tab 49 of cannula release grip 46 contacts stylet push bar 36 thereby moving stylet 34 forward to the position shown by arrow A'. At this point in the procedure, the stylet has penetrated the tissue to the point that the sharpened end of cannula 24 is bearing on the tissue and tissue is then present within sampling notch 31. It is now necessary to advance cannula 24 to slice the tissue projecting into sample notch 31. As indicated in FIG. 4, release trigger 19 is pressed downward as indicated by arrow B. Due to the springiness of spring arms 25, hub stop 13 is moved downward releasing cannula hub 21. Compressed spring 22 snaps cannula hub 21 forward forcing cannula 24 beyond the sampling notch 31 and cleanly slicing the tissue by means of its sharpened end 23. It will be noted that spring 22 is now in the relaxed state in a second forward position. At this point in the procedure, stylet 30 and cannula 20 are both in their maximum forward position. The physician then withdraws the instrument having the desired sample captivated between cannula 24 and notch 31.

It will be noted that guide tube 12 has a sharpened end 11. This permits the physician to insert the entire assembly of the guide tube 12, cannula 20 and stylet 30 into tissue when in the unoperated condition of FIG. 2 to be able to reach an area of suspicion which may not be near the surface.

Having now explained the operation of the instrument, the above-described procedure using one hand will be illustrated with reference to FIGS. 5-7.

While the instrument of the invention is particularly well adapted to transrectal prostate biopsies, there are many other types of biopsies for which one-handed operation is advantageous. For example, it is often necessary for the physician to isolate a suspicious lump or nodule with the fingers with one hand and then produce the desired sampling procedure with the other hand. In the prior art, it is common to require an assistant to perform the isolation function while the physician is utilizing both hands to extract the sample. In such cases, the physician does not have personal control of the procedure. Typical examples of this problem are when biopsies of testicles and breasts are to be performed.

In FIG. 5, the procedure for using the instrument to approach the area to be sampled is shown. Assuming right hand operation, the instrument is gripped in the hand 60 approximately as shown with the index finger 62 placed against the distal end of guide tube 12. For example, when doing a transrectal prostate biopsy, the index finger 52 would be used to locate the suspicious area of the prostate gland and the end of guide tube 12 directed to this point. The physician then pushes the tip of stylet 34 into the tissue until the end of cannula 24 touches the tissue. This completes the first step of the procedure. As will be noted, this portion of the procedure is performed with one hand.

In FIG. 6, the second step is illustrated. The physician moves thumb 64 to rest on grip 42 of arming slide 40 as shown. The thumb is then moved forward as indicated by arrow A until cannula release grips 46 are flush with the proximal end of housing 50, such that locking grooves 47 engage locking tab 17 in housing 50 as best seen in FIG. 8. As illustrated in FIG. 3 above, this cocks cannula spring 22 and advances stylet 30 as indicated by arrow A', completing the second step in the procedure.

The third step is illustrated in FIG. 7 in which the physician moves the thumb from grip 42 to release trigger 19 and pushes downward thereon as indicated by arrow B. This action releases spring 22, causing cannula 24 to snap forward as indicated at arrow B'. This action completes step 3 permitting the physician to then withdraw the instrument from the tissue.

Referring to FIG. 8, to remove the specimen obtained which is in the sampling notch at this point, the operator will squeeze cannula release grips 46a and 46b in the directions of arrows C causing spring arms 45 to move together. As will be also noted from FIG. 8, stylet hub 32 is in the forward position indicating that stylet 34 is fully extended. When cannula release grips 46a and 46b are squeezed together, locking grooves 47 are released from locking tabs 17 and the arming slide 40 may be moved rearwardly, as shown in FIG. 9, withdrawing cannula 24 into guide tube 12 and exposing sampling notch 31, thereby permitting removal of the specimen. The instrument is discarded after removal of the sample.

The biopsy instrument of the invention is specially adapted for one-hand operation. However, it will be apparent that the novel design is advantageous for two-hand use. The physician may approach the tissue to be sampled as shown in FIG. 5. The stylet 30 may be moved forward into the tissue by using the free hand to push on stylet push bar 36 affording the operator full and precise control of penetration. The cannula 20 may then be cocked by pushing the cannula release grips 46 forward with the free hand. The cannula is then advanced by operating trigger 19.

The specific construction of the biopsy instrument shown in the drawings and the above description is for exemplary purposes only. Various modifications in the design of the housing, the spring load cannula, and the triggering element may be made without departing from the spirit and scope of the invention. Although it is preferred that the instrument be disposable, in which case many of the elements may be molded from plastic, it is apparent that the entire instrument may be constructed of metal such as stainless steel to permit sterilization after use and subsequent reuse.

I claim:

1. An improved instrument for biopsies and the like which can be operated with one hand comprising:
   (a) a housing adapted to be held in the palm of a hand of an operator;
   (b) a guide tube extending forward from a distal end of said housing and attached thereto;
   (c) a cutting cannula disposed in said housing and telescopically movable in said guide tube, said cannula having a hub at a proximal end thereof and a cutting distal end extending slightly from a distal end of said guide tube when said cannula is in a retracted position;
   (d) a stylet having a sharpened distal end and a sampling notch adjacent said distal end, said stylet telescopically movable in said cannula in which said distal end extends slightly from the distal end of said cannula when said stylet is in a retracted position;
   (e) a compression spring having a first end engaged with said cannula hub;
   (f) a release spring element having a release trigger and a cannula hub stop, said hub stop being in contact with said hub when said release trigger is non-operated;
   (g) an arming slide slidably disposed in said housing and having a pair of spring blocks in contact with a second end of said compression spring, said arming slide having a first rearward position in which said compression spring is expanded and a second forward position in which said compression spring is compressed, said arming slide also operatively engaged with said stylet to move said stylet from its retracted position when said slide in in said first position to an extended position when said slide is in said second position; and
   (h) said hub stop is released from contact with said hub when said release trigger is operated thereby permitting said compression spring to snap said cutting cannula from its retracted position to an extended position.

2. In a biopsy instrument having a fixed guide tube, a cannula having a sharpened distal end, said cannula telescoped within said guide tube, and a sampling stylet having a sharpened distal end, said stylet telescoped within said cannula, the improvement comprising;
   an elongated housing adapted to be held in the palm of an operator's hand, said guide tube extending from a distal end of said housing;
   a cannula hub attached to a proximal end of said cannula and disposed within said housing;
   a cannula compression spring having a first end engaged with said cannula hub;
   a release spring attached to said housing having a cannula hub stop means for preventing said cannula from extending farther from said guide tube when said release spring is in a first position and for releasing said cannula when said release spring is in a second position;
   an arming slide slidably disposed within said housing and having cannula release grips and locking grooves which extend from a proximal end of said housing, said slide having a spring block in contact with a free second end of said cannula spring, wherein movement of said slide toward said distal end of said housing compresses said cannula spring and said locking grooves lock said cannula spring in a compressed state;
   a stylet hub attached to a proximal end of said stylet, said stylet hub extending from said proximal end of said housing, said cannula release grips coupled to said stylet hub for extending said distal end of said stylet from the distal end of said cannula when said arming slide is moved toward said distal end of said housing; and
   a release trigger attached to said release spring for releasing said compressed cannula spring to cause said distal end of said cannula to extend to said distal end of said stylet.

3. An instrument for performing a biopsy of tissue comprising:
   (a) an elongate housing having a distal end and a proximal end thereof;
   (b) guide tube means attached to said distal end of said housing;
   (c) spring-loaded cannula means having a tubular cutting cannula telescoped within said guide tube means prior to use of said instrument and extendible from a distal end of said guide tube means for cutting a biopsy sample, said spring-loaded cannula means including a cannula hub attached to a proximal end of said cannula, and a compression spring having a first end thereof extending from said hub;
   (d) stylet means including a stylet with a sharpened distal end thereof and a sampling notch adjacent said distal end for captivating said biopsy sample, said stylet telescoped within said cannula prior to use of said instrument and extendible from the distal end of said cannula;
   (e) cannula cocking means for cocking said spring-loaded cannula means and simultaneously extending said stylet from said distal end of said cannula, wherein said housing is adapted to be held in the palm of one of an operator's hand, said guide tube means for permitting the operator to guide the distal end of said stylet to a desired point with an extended finger of said hand, and said cocking means operable by said hand for cocking said cannula and simultaneously extending said distal end of said stylet into said tissue, in which said cannula cocking means includes
  (i) a slide element movably disposed in said housing and having spring blocks for contacting a second end of said compression spring,
  (ii) a thumb grip attached to said slide element and projecting from said housing for moving said slide element to compress said compression spring, and
  (iii) locking means for locking said slide element when said compression spring is compressed; and
(f) trigger means coupled to said spring-loaded cannula means for releasing said cocked spring loaded cannula means to extend said cannula for cutting a tissue sample in said sampling notch, said trigger means operable by said one of said operator's hand, said trigger means including
  (i) a pair of parallel spring arms having proximal ends thereof attached to said housing;
  (ii) a hub stop disposed between said spring arms and contacting said cannula hub when said compression spring is compressed; and
  (iii) a release trigger attached to distal ends of said spring arms and extending from said housing for moving said hub stop thereby releasing said compressed spring.

4. The instrument as defined in claim 3 in which said locking means includes:
  a pair of locking tabs disposed at said proximal end of said housing;
  a pair of cannula release grips attached to a proximal end of said slide element and extending from said proximal end of said housing; and
  said release grips having a pair of locking grooves for engaging said locking tabs for locking said cannula spring in a compressed condition said release grips movable to permit disengagement of said locking grooves from said locking tabs thereby releasing said slide element for withdrawing said cannula after cutting of such biopsy sample.

* * * * *